(12) United States Patent
Grill et al.

(10) Patent No.: US 11,357,983 B2
(45) Date of Patent: Jun. 14, 2022

(54) SYSTEMS AND METHODS FOR APPLYING ELECTRICAL STIMULATION FOR OPTIMIZING SPINAL CORD STIMULATION

(71) Applicant: Duke University, Durham, NC (US)

(72) Inventors: Warren M. Grill, Chapel Hill, NC (US); Tianhe Zhang, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/774,160

(22) PCT Filed: Mar. 13, 2014

(86) PCT No.: PCT/US2014/025423
§ 371 (c)(1),
(2) Date: Sep. 10, 2015

(87) PCT Pub. No.: WO2014/159896
PCT Pub. Date: Oct. 2, 2014

(65) Prior Publication Data
US 2016/0022993 A1 Jan. 28, 2016

Related U.S. Application Data

(60) Provisional application No. 61/779,632, filed on Mar. 13, 2013, provisional application No. 61/779,554, filed on Mar. 13, 2013.

(51) Int. Cl.
*A61N 1/36* (2006.01)
*A61N 1/05* (2006.01)
*G16H 50/50* (2018.01)

(52) U.S. Cl.
CPC ....... *A61N 1/36071* (2013.01); *A61N 1/0551* (2013.01); *A61N 1/36128* (2013.01);
(Continued)

(58) Field of Classification Search
CPC ............ A61N 1/36071; A61N 1/36171; A61N 1/16157; A61N 1/0551; A61N 1/36128
(Continued)

(56) References Cited

U.S. PATENT DOCUMENTS

| 4,338,945 A | 7/1982 | Kosugi et al. |
| 5,716,377 A | 2/1998 | Rise et al. |

(Continued)

FOREIGN PATENT DOCUMENTS

| CN | 102521456 A1 | 6/2012 |
| JP | 2008506464 A | 3/2008 |

(Continued)

OTHER PUBLICATIONS

Notification of Transmittal of the International Search Report and the Written Opinion of the International Searching Authority, or the Declaration, PCT International Searching Authority, dated Aug. 6, 2014.

(Continued)

*Primary Examiner* — Mallika D Fairchild
*Assistant Examiner* — Minh Duc G Pham
(74) *Attorney, Agent, or Firm* — Olive Law Group, PLLC

(57) ABSTRACT

Systems and methods for applying electrical stimulation to different sub-populations of targeted neurological tissue for optimizing spinal cord stimulation are disclosed. According to an aspect, a method includes applying a first pattern of electrical stimulation to a first sub-population of targeted neurological tissue of a subject. The method also includes applying a second pattern of electrical stimulation to a second sub-population of targeted neurological tissue of the subject, the second pattern of electrical stimulation being applied at a different frequency than the first pattern of electrical stimulation.

34 Claims, 13 Drawing Sheets

(52) U.S. Cl.
CPC ..... *A61N 1/36171* (2013.01); *A61N 1/36178* (2013.01); *G16H 50/50* (2018.01)

(58) Field of Classification Search
USPC .......................................................... 607/46
See application file for complete search history.

(56) References Cited

U.S. PATENT DOCUMENTS

| | | |
|---|---|---|
| 6,560,490 B2 | 5/2003 | Grill et al. |
| 6,944,501 B1 | 9/2005 | Pless |
| 7,191,014 B2 | 3/2007 | Kobayashi et al. |
| 7,463,927 B1 | 12/2008 | Chaouat |
| 8,073,544 B2 | 12/2011 | Pless |
| 2002/0052634 A1 | 5/2002 | March |
| 2002/0169563 A1 | 11/2002 | De Carvalho Ferreira |
| 2004/0111127 A1 | 6/2004 | Gliner |
| 2004/0158298 A1 | 8/2004 | Gliner et al. |
| 2005/0060009 A1* | 3/2005 | Goetz ............... A61N 1/36185 607/48 |
| 2005/0222641 A1 | 10/2005 | Pless |
| 2006/0015153 A1 | 1/2006 | Gliner et al. |
| 2006/0149337 A1* | 7/2006 | John .................. A61N 1/36064 607/45 |
| 2007/0191895 A1 | 8/2007 | Foreman |
| 2007/0265679 A1 | 11/2007 | Bradley et al. |
| 2007/0288064 A1 | 12/2007 | Butson et al. |
| 2008/0046036 A1 | 2/2008 | King et al. |
| 2008/0215119 A1 | 9/2008 | Woods |
| 2009/0204173 A1 | 8/2009 | Fang et al. |
| 2009/0279726 A1 | 11/2009 | Baskent |
| 2009/0287271 A1 | 11/2009 | Blum et al. |
| 2009/0326608 A1 | 12/2009 | Huynh et al. |
| 2010/0152807 A1 | 6/2010 | Grill et al. |
| 2010/0152820 A1 | 6/2010 | Grill et al. |
| 2010/0191307 A1* | 7/2010 | Fang .................. A61N 1/36171 607/46 |
| 2011/0040351 A1 | 2/2011 | Butson |
| 2011/0060383 A1 | 3/2011 | Lineaweaver et al. |
| 2011/0087309 A1 | 4/2011 | Stypulkowski |
| 2011/0213442 A1 | 9/2011 | Pless |
| 2012/0136408 A1 | 5/2012 | Grill et al. |
| 2012/0172946 A1* | 7/2012 | Alataris ............. A61N 1/36157 607/46 |
| 2012/0253421 A1 | 10/2012 | Gliner et al. |
| 2013/0006331 A1 | 1/2013 | Weisgarber et al. |
| 2013/0150922 A1 | 6/2013 | Butson et al. |
| 2014/0163640 A1 | 6/2014 | Edgerton et al. |
| 2014/0180361 A1* | 6/2014 | Burdick ............... A61N 1/0553 607/49 |
| 2015/0202446 A1* | 7/2015 | Franke ............... A61B 18/1206 607/48 |

FOREIGN PATENT DOCUMENTS

| | | |
|---|---|---|
| JP | 2011502586 A | 1/2011 |
| JP | 2012-504458 A | 2/2012 |
| WO | 2010/065888 A2 | 6/2010 |

OTHER PUBLICATIONS

Notification of Transmittal of the International Search Report and the Written Opinion of the International Searching Authority, or the Declaration, PCT International Searching Authority, dated Jul. 30, 2014.
Supplementary European Search Report for Application No. EP 14776331 dated Oct. 25, 2016.
USPTO Non-Final Office Action for U.S. Appl. No. 14/774,156 dated Sep. 30, 2016.
Benabid, A., et al, "Long-Term Suppression Of Tremor By Chronic Stimulation Of the Ventral Intermediate Thalamic Nucleus," Lancet. 337:403-6 (Feb. 16, 1991).
Birdno, M.J., "Analyzing the mechanisms of thalamic deep brain stimulation: computational and clinical studies," Ph. D. Dissertation, Department of Biomedical Engineering, Duke University, Durham, NC, USA (Aug. 2009).
Constantoyannis, C., et al, "Tremor induced by thalamic deep brain stimulation in patients with complex regional face pain," Movement Disorders vol. 19, No. 8, 19:933-936. (2004).
Davis, L, "Handbook of Genetic Algorithms" Van Nostrand Reinhold, NY (1991).
Dorval, A. D., et al., "Deep Brain Stimulation Alleviates Parkinsonian Bradykinesia By Regularizing Thalamic Throughput In Human Subjects,". Society for Neuroscience Abstracts 32. (2007), J Neurophysiol 104: 911-921 (Aug. 2010, First published May 26, 2010).
Feng, X., et al, "Optimal Deep Brain Stimulation Of The Subthalamic Nucleus—A Computational Study," J Comput Neurosci. 23(3);265-282 (Jan. 9, 2007).
Final Office Action dated Aug. 10, 2012 in U.S. Appl. No. 12/587,295.
Fogelson, N. et al, "Frequency Dependent Effects Of Subthalamic Nucleus Stimulation In Parkinson's Disease," Neuroscience Letters 382:5-9 (2005).
Grefenstette, J.J., "Optimization of Control Parameters for Genetic Algorithms," IEEE Transactions on Systems, Man and Cybernetics 16:122-128 (1986).
Grill, W.M. et al, "Effect Of Stimulus Waveform On Tremor Suppression And Paresthesias Evoked By Thalamic Deep Brain Stimulation," Society for Neuroscience Abstracts 29 (2003).
International Search Report and the Written Opinion of the International Searching Authority in corresponding PCT application No. PCT/US09/05459 (Dec. 3, 2009).
Kuncel A.M. et al, "Clinical Response To Varying The Stimulus Parameters In Deep Brain Stimulation For Essential Tremor," Movement Disorders 21(11):1920-1928 (2006).
Kupsch, A. et al, "The effects of frequency in pallidal deep brain stimulation for primary dystonia," J Neurol 250:1201-1204 (2003).
Limousin, P. et al., "Effect on Parkinsonian signs and symptoms of bilateral stimulation," The Lancet 345:91-95 (1995).
McIntyre, C.C., et al., "Cellular effects of deep brain stimulation: model-based analysis of activation and inhibition," J Neurophysiol 91:1457-1469 (2004).
Non-Final Office Action dated Mar. 9, 2012 in U.S. Appl. No. 12/587,295.
Notice of Allowance dated Apr. 15, 2013 in U.S. Appl. No. 12/587,295.
Rubin, J.E. et al, "High Frequency Stimulation Of the Subthalamic Nucleus Eliminates Pathological Thalamic Rhythmicity In A Computational Model,". J Comput Neurosci 16:211-235 (2004).
Timmerman, L. et al, "The cerebral oscillatory network of parkinsonian resting tremor," Brain, 126:199-212 (2003).
Supplementary European Search Report for Application No. EP 14773114, PCT/US2014025389 dated Nov. 3, 2016.
Australian Examination Report for Application No. 2014244386 dated Jul. 24, 2017.
U.S. Non-Final Office Action for U.S. Appl. No. 14/774,156 dated Aug. 16, 2017.
Extended European Search Report dated Nov. 3, 2016, received in EP Application No. 14776331.2.
Final Office Action received in U.S. Appl. No. 14/774,156 dated Apr. 14, 2017.
Office Action received in U.S. Appl. No. 14/774,156 dated Sep. 30, 2016.
International Search Report and Written Opinion issued in PCT Application No. PCT/US2017/035556 dated Oct. 2, 2017.
Office Action for Japanese Patent Application No. JP 2016-501846 dated Feb. 27, 2018 (six (6) pages).
European Search Report and Opinion for European Patent Application No. 15814864.3 dated Jan. 8, 2018.
Office Action for Japanese Patent Application No. JP 2016-501841 dated Jan. 9, 2018.
Non-Final Office Action for U.S. Appl. No. 15/321,801 dated Feb. 5, 2018.
Decision of Refusal issued in counterpart Japanese Patent Application No. JP 2016-501846 dated Nov. 6, 2018 (four (4) pages).

(56) References Cited

OTHER PUBLICATIONS

Notice of Allowance issued in counterpart U.S. Appl. No. 14/774,156 dated Dec. 11, 2018.
International Preliminary Report on Patentability and Written Opinion issued in PCT Application No. PCT/US2017/035556 dated Dec. 4, 2018 (eight (8) pages).
Final Office Action issued in counterpart U.S. Appl. No. 14/774,156 dated May 7, 2018.
Notice of Acceptance issued in counterpart Australian Application No. 2014244386 dated May 11, 2018 (three (3) pages).
Second Office Action issued in counterpart Japanese Application No. 2016-501841 dated May 15, 2018 with English translation (eighteen (18) pages).
Australian Examination Report issued in counterpart Australian Application No. 2014244318 dated May 20, 2018 three (3) pages).
Notice of Allowance issued in counterpart U.S. Appl. No. 15/321,801 dated May 25, 2018.
Decision of Refusal issued in counterpart Japanese Patent Application No. JP 2016-501841 dated Mar. 18, 2019 (two (2) pages).
Examination Report issued in counterpart Australian Application No. 2018217227 dated Jul. 16, 2019 (three (3) pages).
Notice of Allowance issued in counterpart U.S. Appl. No. 14/774,156 dated Dec. 26, 2018.
Communication under Rule 71(3) EPC issued in counterpart European Patent Application No. 15814864.3 dated Sep. 25, 2019 (fifty-nine (59) pages).
Nonfinal Office Action in related U.S. Appl. No. 16/303,812 dated Feb. 17, 2021, (6 pages).
Foreign Office Action in related Canadian application 2,905,004 filed Sep. 9, 2015, dated Mar. 4, 2021. (4 pages).
Decision of Refusal issued in counterpart Japanese Patent Application No. JP 2016-501841 filed Sep. 11, 2015, dated Mar. 18, 2019. (1 page).
English ranslation of Decision of Refusal issued in counterpart Japanese Patent Application No. JP 2016-501841 filed Sep. 11, 2015, dated Mar. 18, 2019. (1 page).
Canadian Examiner Search Report in counterpart Canadian Patent Application No. 2905102 filed Sep. 9, 2015, dated Apr. 16, 2021. (4 pages).
Examination Report No. 2 issued in related Australian Application No. 2020205274 dated Nov. 22, 2021. (4 pages).
Examination Report No. 1 issued in related Australian Application No. 2020205274 dated Jul. 19, 2021. (3 pages).
Intention to Grant issued in related European Application No. 14776331.2 dated Apr. 1, 2021. (38 pages).
Intention to Grant issued in associated European Application No. 14773114.5 dated Apr. 1, 2021. (39 pages).
Notice of Allowance issued in related U.S. Appl. No. 16/303,812 dated Jun. 21, 2021. (6 pages).

* cited by examiner

SYSTEMS AND METHODS FOR APPLYING ELECTRICAL STIMULATION FOR OPTIMIZING SPINAL CORD STIMULATION

CROSS REFERENCE TO RELATED APPLICATIONS

This application is a 371 USC 371 application of PCT International Patent Application No. PCT/US2014/025423, filed Mar. 13, 2014 and titled SYSTEMS AND METHODS FOR APPLYING ELECTRICAL STIMULATION FOR OPTIMIZING SPINAL CORD STIMULATION, which claims priority to U.S. Provisional Patent Application No. 61/779,632, filed Mar. 13, 2013 and titled SYSTEMS AND METHODS FOR OPTIMIZING SPINAL CORD STIMULATION, and U.S. Provisional Patent Application No. 61/779,554, filed Mar. 13, 2013 and titled SYSTEMS AND METHODS FOR OPTIMIZING SPINAL CORD STIMULATION; all of the contents of which are hereby incorporated by reference herein in their entireties. This application is related to co-owned U.S. patent application Ser. No. 14/774,156, titled SYSTEMS AND METHODS FOR ADMINISTERING SPINAL CORD STIMULATION BASED ON TEMPORAL PATTERNS OF ELECTRICAL STIMULATION, and filed simultaneously.

TECHNICAL FIELD

The presently disclosed subject matter relates to spinal cord stimulation, and more specifically, to applying electrical stimulation for optimizing spinal cord stimulation (SCS).

BACKGROUND

SCS has emerged as a therapy for chronic pain when kinetic (e.g., physical rehabilitation), pharmaceutical, and surgical therapies have not been effective. However, between 1974 and 1991, according to studies the clinical success of SCS has been highly variable, with a mean of 54.2% and a standard deviation of 20%, and subsequent studies have shown very little improvement. Efforts to improve the clinical efficacy of SCS have focused on the development of more spatially selective electrodes, while only minimal attention has been paid to the temporal patterning of SCS or the effects of SCS on the activity of neurons in the dorsal horn pain processing circuit. Although there have been advances in SCS, there is a continuing need for improved techniques and systems for optimizing SCS.

BRIEF SUMMARY

Disclosed herein are systems and methods for applying electrical stimulation to different sub-populations of targeted neurological tissue for optimizing spinal cord stimulation. According to an aspect, a method includes applying a first pattern of electrical stimulation to a first sub-population of targeted neurological tissue of a subject. The method also includes applying a second pattern of electrical stimulation to a second sub-population of targeted neurological tissue of the subject, the second pattern of electrical stimulation being applied at a different frequency than the first pattern of electrical stimulation. Further, the method includes controlling the first and second patterns of electrical stimulation for optimizing suppression of activity of wide-dynamic range (WDR) neurons to improve the efficacy of stimulation and/or reducing the average stimulation frequency to improve the efficiency of stimulation.

BRIEF DESCRIPTION OF THE SEVERAL VIEWS OF THE DRAWINGS

The foregoing aspects and other features of the present subject matter are explained in the following description, taken in connection with the accompanying drawings, wherein.

DETAILED DESCRIPTION

Figure 1:
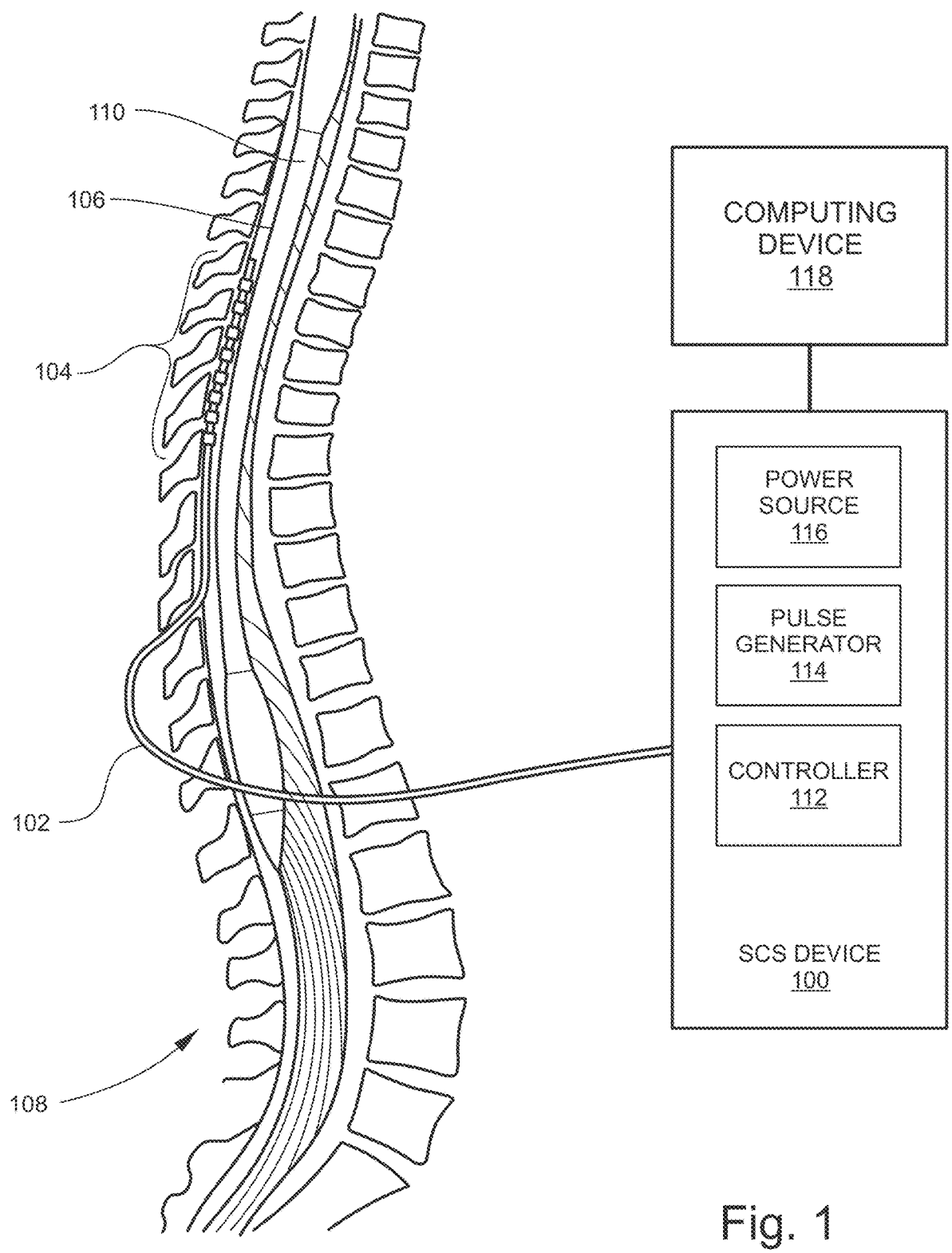
FIG. 1 is an anatomic view of a system for stimulating targeted neurological tissue of a human subject in accordance with embodiments of the present disclosure.

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

As used herein, the term "subject" and "patient" are used interchangeably herein and refer to both human and non-human animals. The term "non-human animals" of the disclosure includes all vertebrates, e.g., mammals and non-mammals, such as non-human primates, sheep, dog, cat, horse, cow, chickens, amphibians, reptiles, and the like. In examples provided herein, the subject is a human patient in need of spinal cord stimulation.

As used herein, the term "neurological disorder" refers to any pathological condition relating to the brain and/or nervous system. Examples include, but are not limited to, pain, which includes chronic and acute neuropathic pain, migraine, trauma, and the like. As used herein, the term "pain" refers to the basic bodily sensation induced by a noxious stimulus, received by naked nerve endings, characterized by physical discomfort (e.g., pricking, throbbing, aching, etc.) and typically leading to an evasive action by the individual. As used herein, the term pain also includes chronic and acute neuropathic pain. The term "chronic pain" and "chronic neuropathic pain" are used interchangeably refer to a complex, chronic pain state that is usually accompanied by tissue injury wherein the nerve fibers themselves may be damaged, dysfunctional, or injured. These damaged nerve fibers send incorrect signals to other pain centers. The impact of nerve fiber injury includes a change in nerve function both at the site of injury and areas around the injury. Chronic neuropathic pain often seems to have no obvious cause, however, some common causes may include, but are not limited to, alcoholism, amputation, back, leg and hip problems, chemotherapy, diabetes, facial nerve problems, HIV infection or AIDS, multiple sclerosis, shingles, spine injury, and the like. For example, neuropathic pain may include phantom limb syndrome, which occurs when an arm or leg has been removed because of illness or injury, but the brain still gets pain messages from the nerves that originally carried impulses from the missing limb.

As referred to herein, the term "administering" refers to the delivery of an electrical impulse/signal/frequency to a subject to thereby cause stimulation to a nerve, nerve fiber, or group of nerve fibers. For example, electrical impulse/ signal/frequency may be applied by use of one or more electrodes in electrical communication with a targeted neurological tissue region, such as sub-populations of dorsal column nerve fibers for example.

Unless otherwise defined, all technical terms used herein have the same meaning as commonly understood by one of ordinary skill in the art to which this disclosure belongs.

In accordance with embodiments of the present disclosure, systems and methods of optimizing SCS are disclosed. A system for delivering SCS to a subject can include a pulse generator. The pulse generator may be configured to generate electrical signals for delivery to targeted neurological tissue of the subject. The system may also include one or more SCS electrodes in electrical communication with an output of the pulse generator. The contact(s) may be placed in contact with the targeted neurological tissue. A controller of the system may control the pulse generator to produce predetermined patterns of electrical stimulation to the targeted neurological tissue. The patterns may be controlled based on prior simulations that optimized suppression of activity of model wide-dynamic range (WDR) neurons to improve the efficacy of treatment. The pattern may be controlled to reduce the average stimulation frequency to improve the efficiency of treatment.

FIG. 1 illustrates an anatomic view of a system for stimulating targeted neurological tissue of a human subject in accordance with embodiments of the present disclosure. The subject may be suffering from a neurological disorder, such as chronic pain. Referring to FIG. 1, the system includes an SCS device 100, an electrical cord 102 and an electrode array generally designated 104. The system is shown as being implanted in the subject. Particularly, the electrode array 104 is operatively positioned in the epidural space 106 of a vertebral column 108 of the subject. The electrode array 104 is positioned at the site of nerves that are the target of stimulation, e.g., along the spinal cord 110. Alternatively, the electrode array 104 may be suitably positioned in any other location for desired electrical stimulation of targeted neurological tissue. The cord 102 may include multiple lines or fibers such that different or the same electrical signals can be provided to contacts of the electrode array 104. The SCS device 100 may be suitably implanted within the subject such as, but not limited to, implantation within the abdomen or buttocks. The electrical cord 102 may operatively connect an output of the SCS device 100 to the electrode array 104.

The SCS device 100 may include a controller 112 and a pulse generator 114. The controller 112 may include hardware, software, firmware, or combinations thereof for implementing functionality described herein. For example, the controller 112 may be implemented by one or more processors and memory. The controller 112 may be operatively connected to the pulse generator 114 for controlling the pulse generator 114 to generate electrical signals for applying patterns of electrical stimulation to targeted neurological tissue. The output signals may be received by the electrical cord 102 and carried to the electrode array 104 for electrical stimulation at targeted neurological tissue. The SCS device 100 may include a power source 116, such as a battery, for supplying power to the controller 112 and the pulse generator 114.

The system may also include an external computing device 118 that is not implanted within the subject. The computing device may communicate with the SCS device 100 via any suitable communication link (e.g., a wired, wireless, or optical communication link). The communication link may also facility battery recharge. A clinician may interact with a user interface of the computing device for programming the output of the implanted pulse generator 114, including the electrodes that are active, the stimulation pulse amplitude, the stimulation pulse duration, the stimulation pattern (including pulse repetition frequency), and the like applied via each electrode contact to each sub-population.

Further, in accordance with embodiments of the present disclosure, the computing device 118 may determine one or more non-regular temporal patterns that results in predetermined WDR neuronal output and stimulation activity. The computing device 118 may communicate information for administering the temporal patterns to the SCS device 100, which may then apply the non-regular temporal pattern(s) of electrical stimulation to targeted neurological tissue of the subject.

A patient may also interact with the user interface of the computing device 118. In this embodiment, the patient may interact with the user interface for selecting among a set of pre-programmed stimulation parameter sets. These sets may have been programmed or otherwise set by the clinician and stored in the controller 112.

Figure 2:
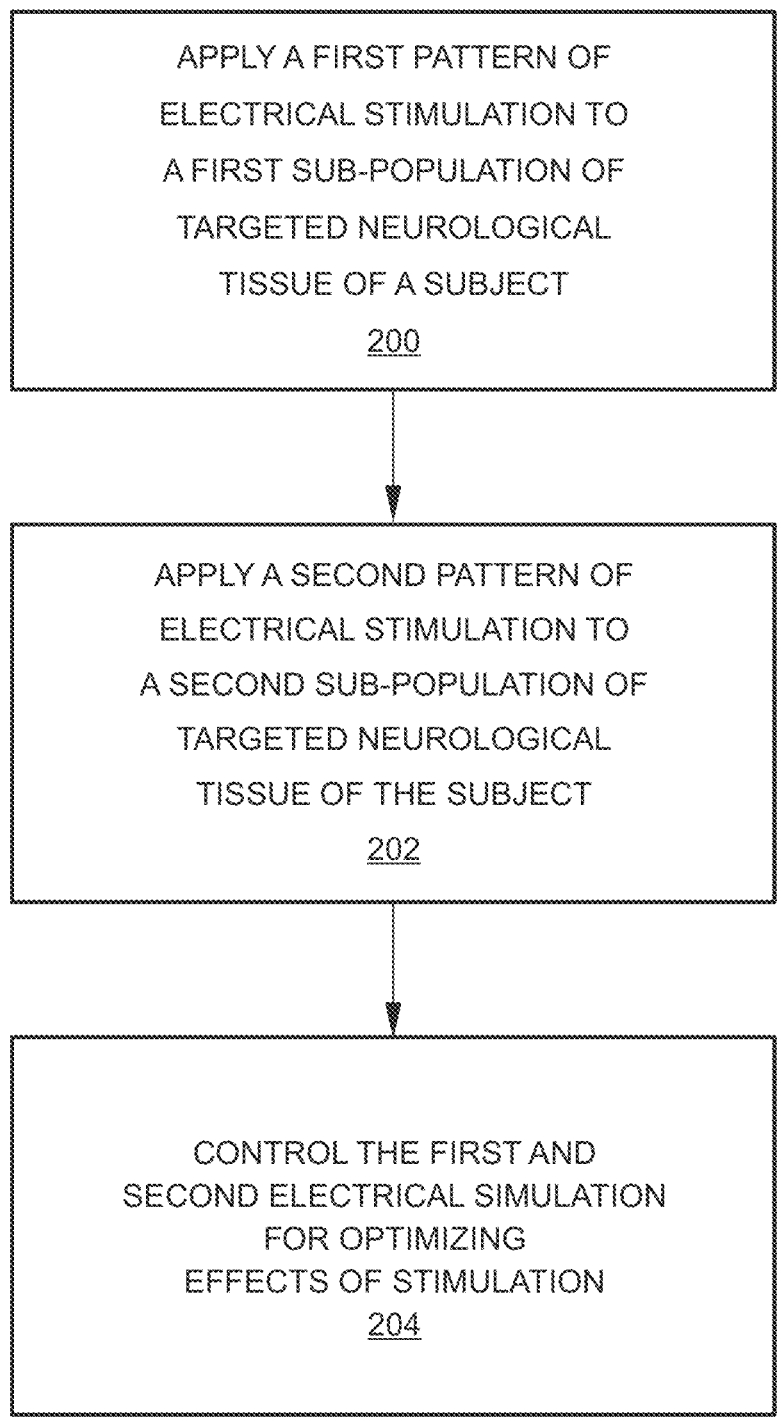
FIG. 2 is a flow chart of an example method for SCS in accordance with embodiments of the present disclosure.

FIG. 2 illustrates a flow chart of an example method for SCS in accordance with embodiments of the present disclosure. The example method is described as being implemented by the system and configuration shown in FIG. 1, although it should be understood that the method may alternatively be implemented by any other suitable system in any other suitable configuration.

Referring to FIG. 2, method includes applying 200 a first pattern of electrical stimulation to a first sub-population of targeted neurological tissue of a subject. For example, the controller 112 may be configured to control the pulse generator 114 to generate electrical signals that produce a predefined pattern of electrical stimulation to a particular sub-population of dorsal column nerve fibers. One or more contacts of the electrode array 104 may be placed in electrical communication and in position to apply the electrical stimulation to the sub-population of dorsal column nerve fibers. The pattern of electrical stimulation may include regular temporal patterns of stimulation (i.e., constant inter-pulse intervals) or non-regular temporal patterns of stimulation (i.e., interpulse intervals that vary in time).

The method of FIG. 2 includes applying 202 a second pattern of electrical stimulation to a second sub-population of targeted neurological tissue of the subject. It should be noted that steps 200 and 202 may occur simultaneously or one after the other. The second pattern of electrical stimulation may be applied at a different frequency than the first pattern of electrical stimulation. For example, the controller 112 may be configured to control the pulse generator 114 to generate electrical signals that produce a predefined pattern of electrical stimulation to another sub-population of dorsal column nerve fibers. Another one or more contacts of the electrode array 104 may be placed in electrical communication and in position to apply the electrical stimulation to the other sub-population of dorsal column nerve fibers. The pattern of electrical stimulation may be applied at multiple different frequencies and at different timings. Further, for example, the patterns may be applied at different frequencies that are multiples of each other. The patterns may include regular temporal patterns of stimulation (i.e., constant interpulse intervals) or non-regular temporal patterns of stimulation (i.e., interpulse intervals that vary in time).

The method of FIG. 2 includes controlling 204 the first and second patterns of electrical stimulation for optimizing the effects of stimulation. For example, the patterns may optimize suppression of activity of WDR neurons and thereby achieve pain relief. For example, the controller 112 may control the pulse generator 114 to output electrical signals to the electrode array 104 for optimizing suppression of activity of WDR neurons. In an example, the controller 112 may implement an algorithm for optimization. In another example, the controller 112 may receive user input for control of the application of the patterns of electrical stimulation.

Figure 3:
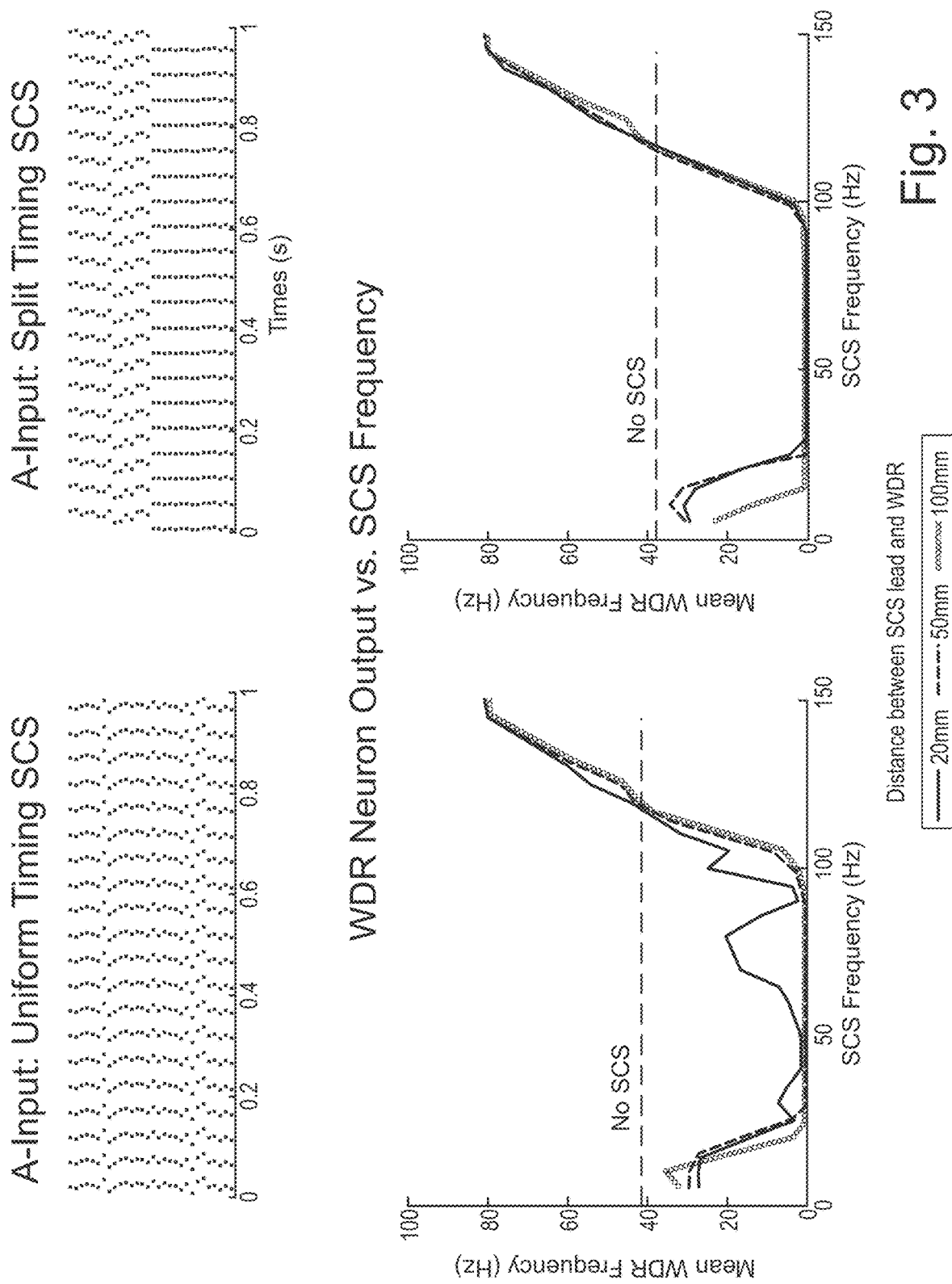
FIG. 3 are graphs showing that delivering SCS at different timings through different fiber populations can result in greater efficacy in response to a 1 Hz peripheral input.

In accordance with embodiments, systems disclosed herein may provide multi-frequency, multi-fiber SCS for achieving suppression of nociceptive information from the spinal cord. Computational modeling work indicated that the activity of WDR neurons in the spinal cord that transmit nociceptive information (i.e., pain signals) to the brain can be better suppressed by stimulation of sub-populations of dorsal column nerve fibers at different timings than by uniform stimulation at the same equivalent frequency. For example, FIG. 3 illustrates graphs showing that delivering SCS at different timings through different fiber populations can result in greater efficacy in response to a 1 Hz peripheral input. Referring to FIG. 3, SCS applied using the two population input set denoted in the right reduces the activity of the WDR neurons responsible for relaying nociceptive (pain) information to the brain to a greater extent and over a wider frequency range than application of SCS using the uniform input set denoted on the left across several simulated positions of the SCS electrode relative to the WDR neuron. The dotted line denotes the average frequency of the WDR neuron's activity when no SCS was applied. This finding indicates that delivering multiple frequencies of SCS to multiple sub-populations of dorsal fibers will yield more effective (reduction in WDR firing) or more efficient (fewer SCS pulses delivered, and thereby less power consumption) SCS than constant frequency stimulation.

Figure 4:
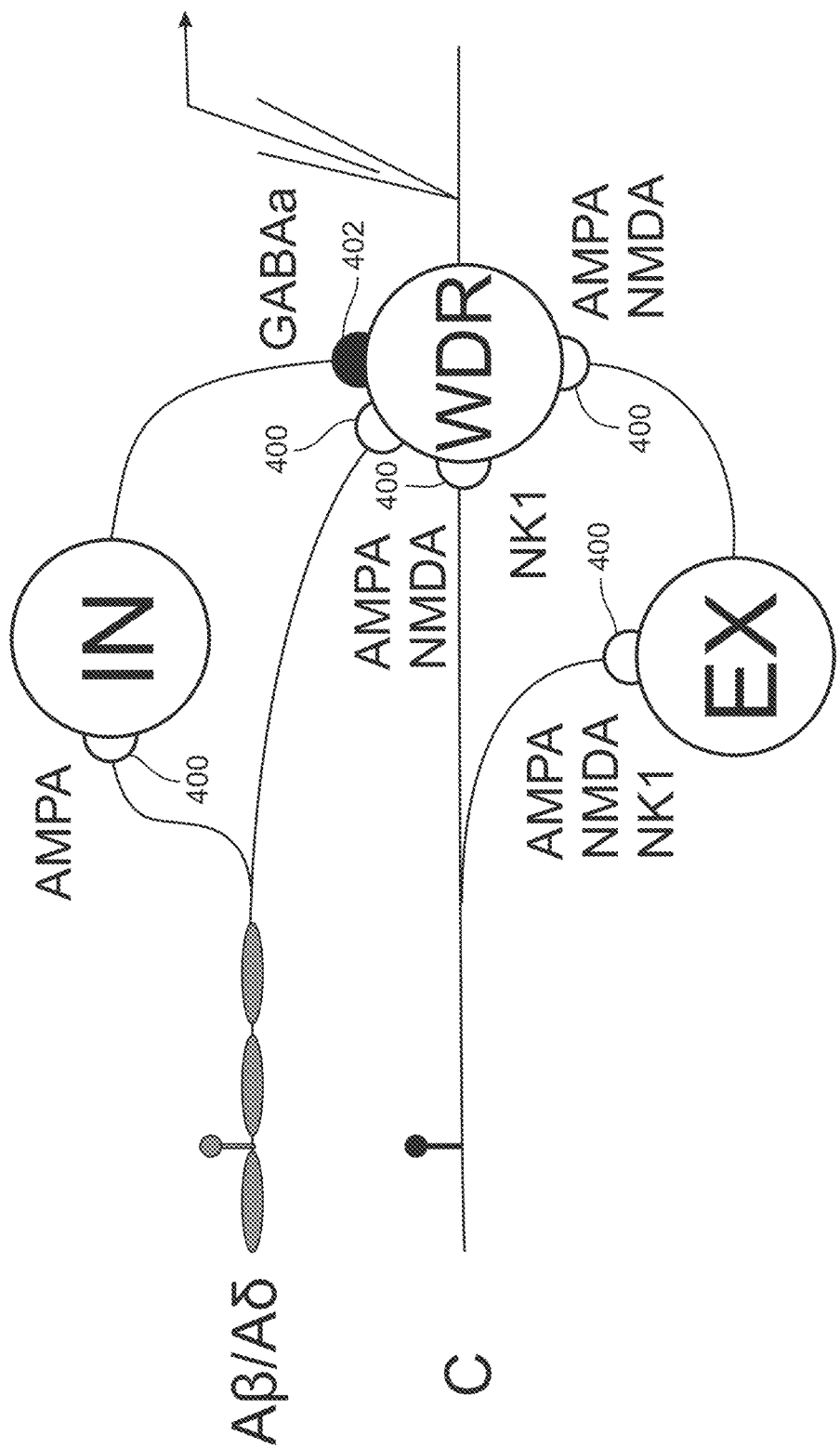
FIG. 4 is a schematic of an example computational model for model-based design and evaluation of optimal temporal patterns of SCS.

FIG. 4 illustrates a schematic of an example computational model for model-based design and evaluation of patterns of SCS. Referring to FIG. 4, the computational model may include a network of biophysical neurons that are connected to represent a dorsal horn pain processing network. Inputs to the model include 30 A and 30 C primary afferent fibers that convey information from the periphery, and SCS may be delivered to the network via the A fibers to simulate dorsal column fiber activation. Multiple A/C fibers and excitatory interneurons may be used to account for the effects of temporal summation on neuronal activity as well as to add variability to the inputs. In addition, to simulate realistic signal propagation from a peripheral or dorsal column nerve fiber, propagation delays based on the conduction velocities of A and C fibers may be incorporated into all inputs for all simulations. In FIG. 4, the "IN" node represents inhibitory interneuron, the "EX" node represents excitatory interneuron, the "WDR" node represents WDR projection neurons. Synapses 400 denote excitatory connections. Synapse 402 denotes an inhibitory connection. SCS using the optimization algorithm may be delivered via the A-fiber input.

Figure 5A:
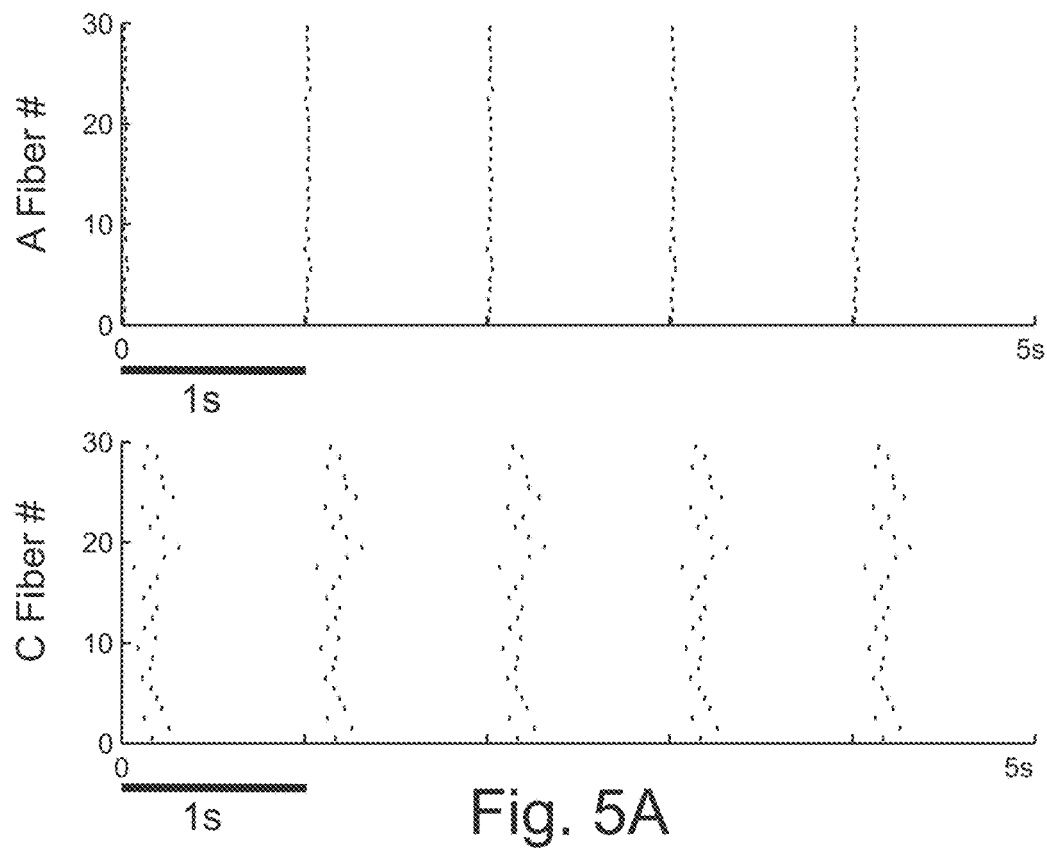
FIGS. 5A and 5B are graphs showing example patterns of activity in peripheral primary afferent fibers.
Figure 5B:
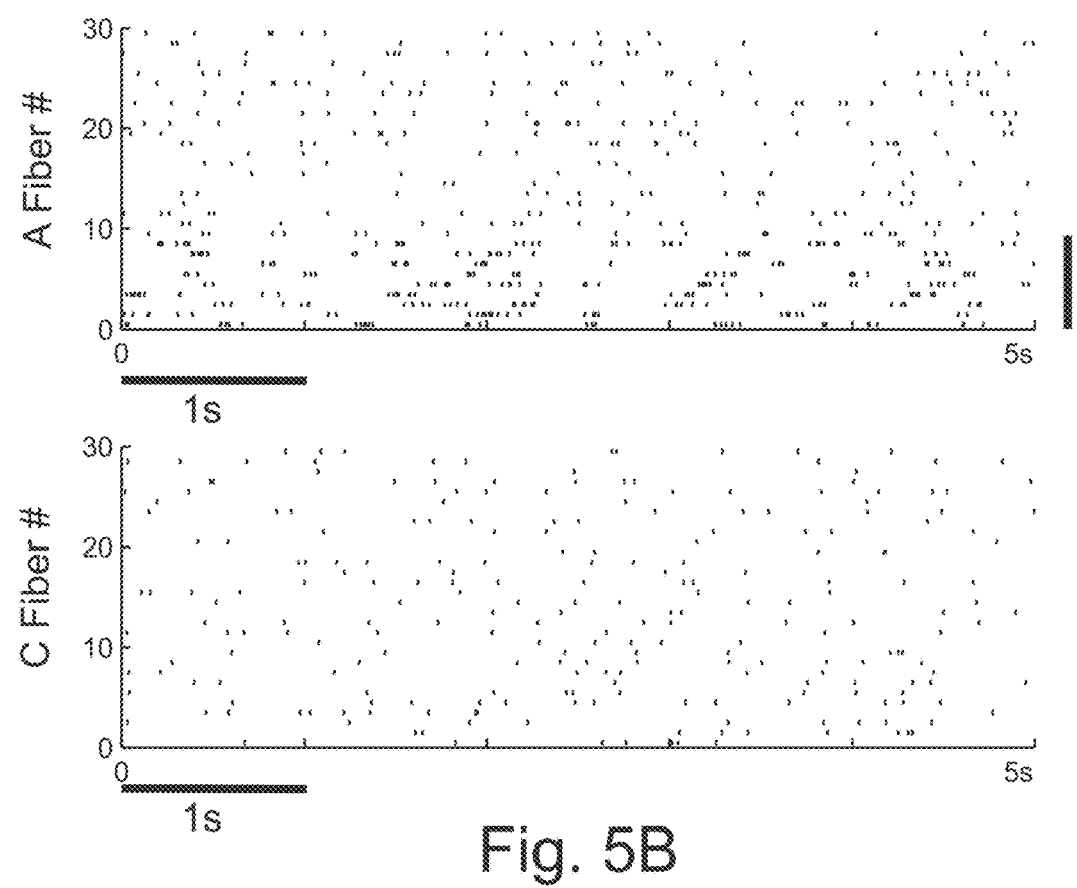

FIGS. 5A and 5B illustrate graphs showing example patterns of activity in peripheral primary afferent fibers. Referring to FIG. 5A, the graphs show representative uniform 1 Hz inputs. FIG. 5B shows randomized inputs representing a neuroma. A 5-second interval (x-axis) of each is shown for all fiber inputs (y-axis; split by A and C fibers). Each black dot on the graph represents a time point at which a spike is registered by a corresponding input to the model. In FIG. 5B, 30% of the A-fiber inputs exhibit bursting behavior. During multi-frequency SCS, the bursty inputs were split such that half of these inputs received one frequency of stimulation while the other half received the other frequency.

Figure 6A:
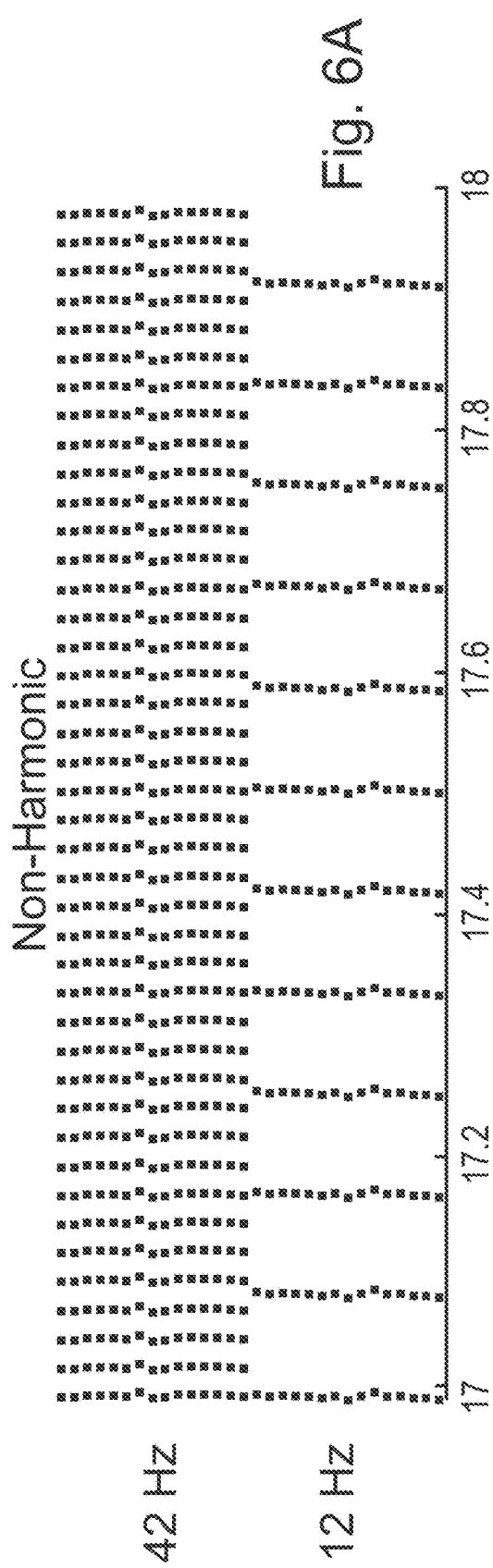
FIGS. 6A and 6B are graphs showing 1-second long examples of non-harmonic and harmonic multi-frequency SCS, respectively.
Figure 6B:
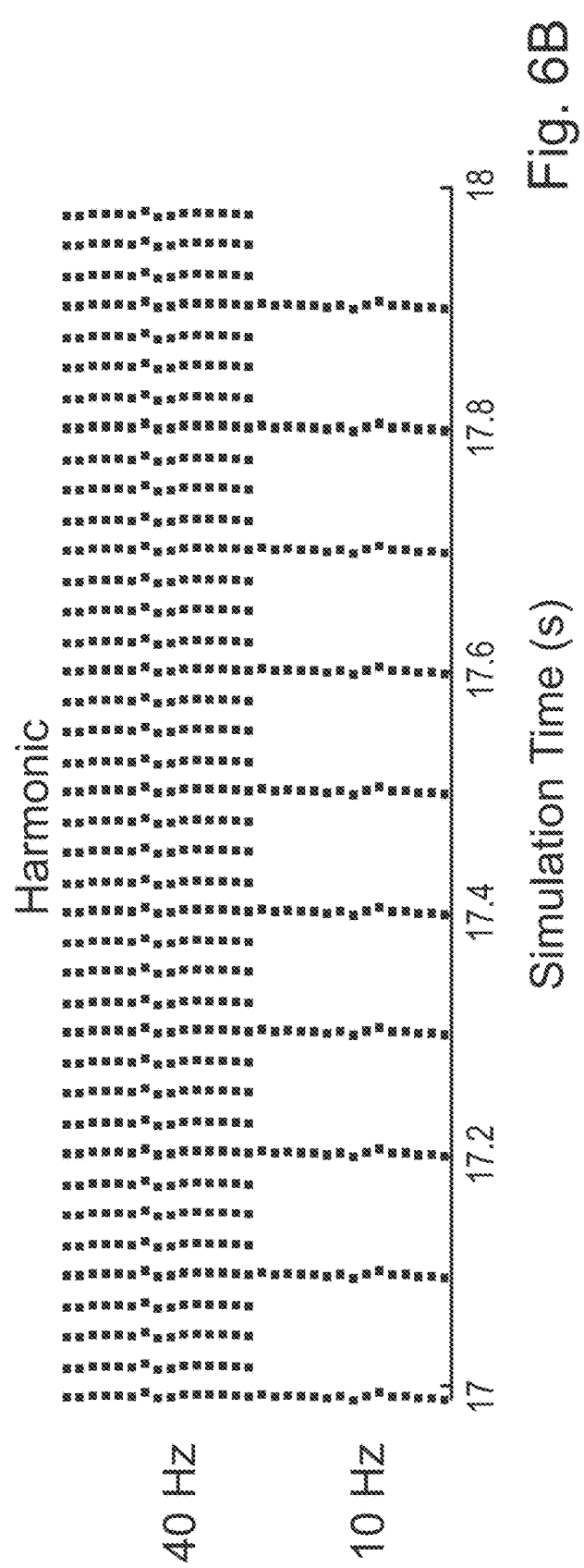

Computational experiments were conducted to demonstrate the utility of the present subject matter. For example, FIGS. 6A and 6B illustrate graphs showing 1-second long examples of non-harmonic (i.e., a first stimulation frequency applied to subpopulation one and a second stimulation frequency applied to subpopulation two were not integer multiples of one another) and harmonic (i.e., a first stimulation frequency applied to subpopulation one and a second stimulation frequency applied to subpopulation two were integer multiples of one another) multi-frequency SCS, respectively. Briefly, one second of simulation time was allowed to elapse to allow the model to initialize, and periphery sensory input including either a constant 1 Hz pulse train synchronized across all fibers or a random spike train based on a Poisson process whose characteristics match those taken from the firing behavior of a peripheral neuroma (as shown in FIGS. 5A and 5B) was then delivered for 15 seconds. SCS using two frequencies—with half of the input A fibers receiving one frequency (a first subpopulation receiving a first stimulation frequency) and the other half receiving the other frequency (a second subpopulation receiving a second stimulation frequency)—was then delivered for the remaining 5 seconds while the output of the WDR neuron was recorded; these frequencies may be harmonic or non-harmonic (see FIG. 7 for example). In harmonic multi-frequency SCS, the higher frequency of stimulation (40 Hz) was set to be an integer multiple of the lower frequency of stimulation (10 Hz). In non-harmonic multi-frequency SCS, the lower frequency was drawn from a uniform random distribution ranging from 40 Hz to 50 Hz and checked to ensure that the higher frequency was not an integer multiple of the lower frequency. The output of the WDR neuron as well as the number of pulses used during stimulation were compared with the corresponding metrics resulting from the first lower frequency SCS delivered to all A fibers, the average of the two applied frequencies delivered to all A fibers, and the second higher frequency delivered to all A fibers. In FIGS. 6A and 6B, each black dot on the graphs represent a time point at which an SCS spike is fed into an A-fiber unit to the computational model during a time period shown in FIG. 7, which illustrates a timeline of each experimental run in accordance with embodiments of the present disclosure. In both the non-harmonic and harmonic cases, half of the A-fibers receive the lower frequency while the other half of the A-fibers receive the higher frequency.

Figure 7:
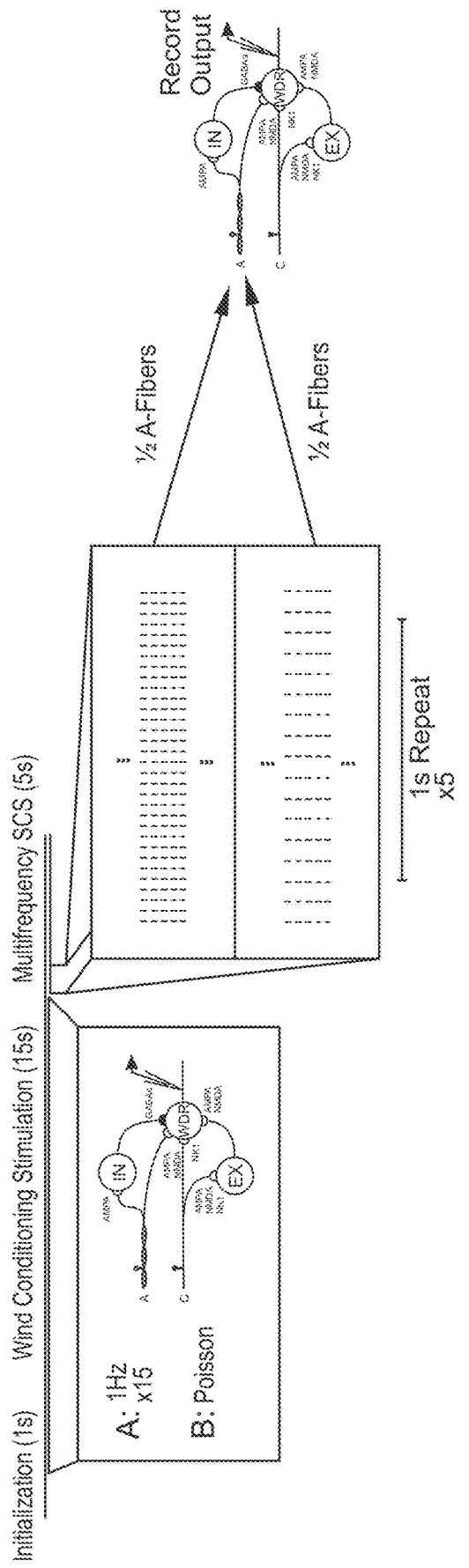
FIG. 7 is a timeline of each experimental run in accordance with embodiments of the present disclosure.

Referring to FIG. 7, SCS is delivered following a brief model initialization period and 15 seconds of conditioning stimulation using either constant 1 Hz or randomized inputs similar to those recorded from neuromas in live preparations. The output of the WDR neuron as well as the average frequency of SCS delivered—a measure of power consumption—are used to gauge respectively the efficacy and efficiency of multi-frequency SCS (i.e., a first stimulation frequency applied to a first subpopulation of nerve fibers and a second stimulation frequency applied to second subpopulation of nerve fibers) versus conventional SCS (one stimulation frequency delivered to all nerve fibers).

Figure 8:
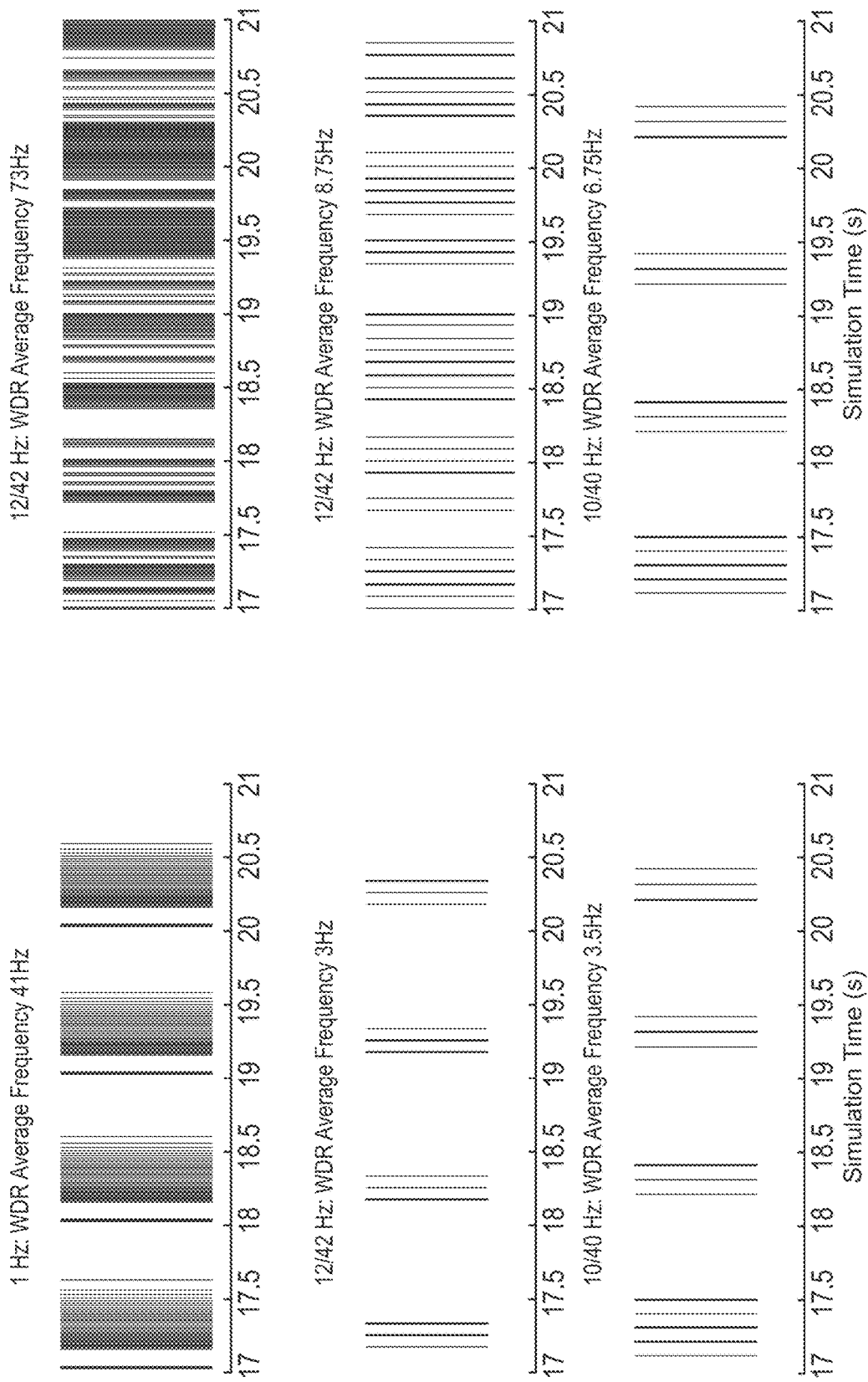
FIG. 8 are Raster plots depicting example activity of a WDR neuron during the period of time in which multi-frequency SCS may be delivered.

In experimentation, it has been shown that the techniques and systems disclosed herein are effective at suppressing WDR neuron behavior and efficient with respect to pulses delivered (power consumption) versus high frequency stimulation through testing of the prototype algorithm using a computational model of pain. In the experiments, it was shown that the application of non-harmonic and harmonic multi-frequency SCS inhibits the activity of the WDR neuron compared to the case in which no SCS was applied. The application of 12 Hz/42 Hz non-harmonic SCS reduced the activity of the WDR neuron by 92.7% in response to a 1 Hz input (41 Hz to 3 Hz) and by 88.0% (73 Hz to 8.8 Hz) in response to a neuropathic input. Application of 10 Hz/50 Hz harmonic SCS reduced the activity of the WDR neuron by 91.5% (41 Hz to 3.5 Hz) in response to a 1 Hz input and by 90.8% (73 Hz to 6.75 Hz) in response to a neuropathic input. For example, FIG. 8 illustrates raster plots depicting example activity of a WDR neuron, such as shown in FIG. 4, during the period of time in which multi-frequency SCS may be delivered. Referring to FIG. 8, each blank line on the graph represents a time point at which a spike is output by the WDR neuron. The top row depicts the activity of the WDR neuron in response to the 1 Hz input and the neuropathic input during no SCS. The middle row depicts the activity of the WDR neuron in response to these inputs during non-harmonic (12 Hz/42 Hz) multi-frequency SCS. The bottom row depicts the activity of the WDR neuron in response to these inputs during harmonic frequency (10 Hz/42 Hz) multi-frequency SCS.

Figure 9:
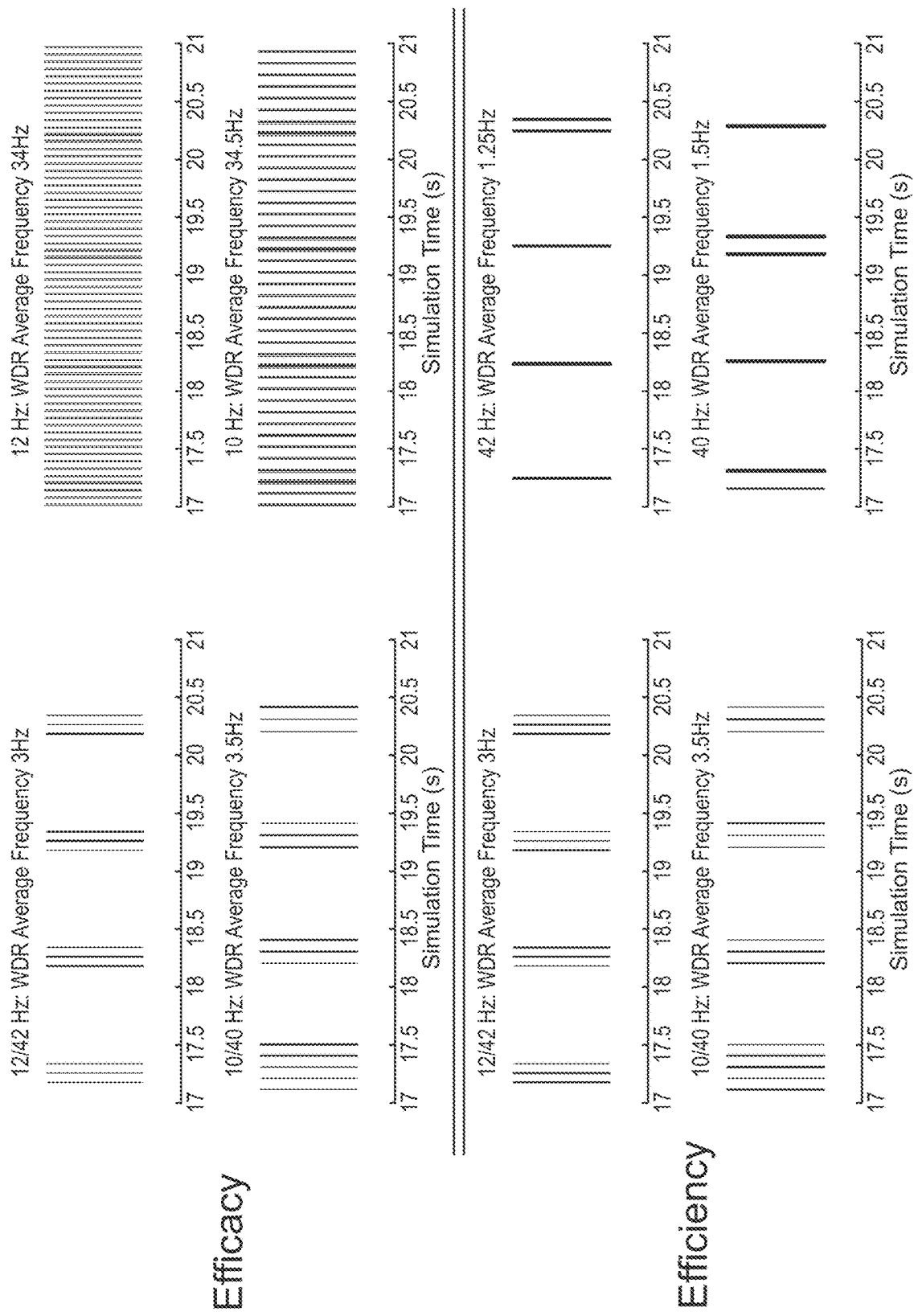
FIG. 9 are Raster plots depicting comparisons of SCS efficacy and efficiency between multi-frequency SCS and conventional SCS at fixed frequency in response to a 1 Hz conditioning input.

Further, in experimentation, it was demonstrated that both non-harmonic SCS and harmonic SCS are more effective at suppressing WDR neuronal activity versus single frequency stimulation at low frequencies and more efficient at suppressing WDR neuronal activity versus single frequency stimulation at high frequencies during a 1 Hz peripheral input. For example, FIG. 9 illustrates raster plots depicting comparisons of SCS efficacy and efficiency between multi-frequency SCS and conventional SCS at fixed frequency in response to a 1 Hz conditioning input. Each black line represents a time point at which a spike is output by the WDR neuron. The output from a given pair of stimulation frequencies is compared to the output due to the stimulation at the lower frequency (12 Hz, 10 Hz—top) and higher frequency (42 Hz, 40 Hz—bottom). Both non-harmonic and harmonic SCS significantly reduce the activity of the WDR neuron versus constant frequency stimulation at the lower frequency (top of FIG. 9) in response to a 1 Hz input (92.7% vs. 17.1%—non-harmonic; 90.8% vs. 15.9%—harmonic). Although simulation using the higher frequency reduces the activity of the WDR neuron to a slightly greater degree, multi-frequency SCS is able to achieve comparable results (92.7% non-harmonic and 90.8% harmonic reduction vs. 97.0% and 96.3% reduction during respective single frequency stimulation) using an average frequency that is 15 Hz lower than the higher frequency of SCS (27 Hz vs. 42 Hz non-harmonic; 25 Hz vs. 40 Hz harmonic), corresponding to 35.7% (non-harmonic) and 37.5% (harmonic) less power used if stimulation frequency is taken as a direct measure of power consumption (bottom of FIG. 9).

Figure 10:
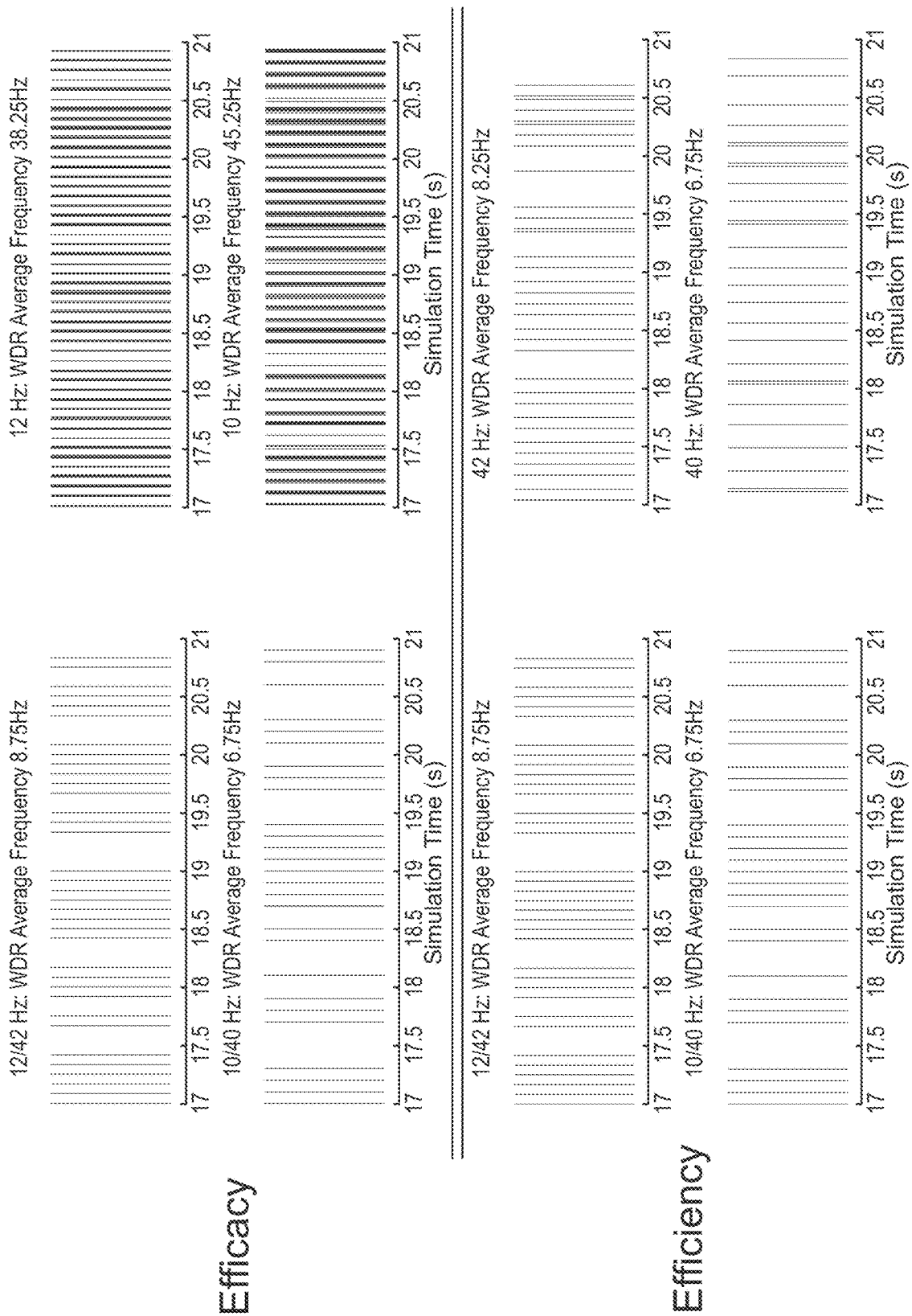
FIG. 10 are Raster plots depicting comparisons of SCS efficacy (WDR neuronal output) and efficiency (average stimulation frequency) between multi-frequency SCS and conventional SCS at a fixed frequency in response to a neuropathic input.

The trends observed above hold when SCS was applied during a neuropathic input to the computational model as well. Both non-harmonic and harmonic SCS significantly reduce the activity of the WDR neuron versus constant frequency stimulation at the lower (88.0% vs. 47.7%—non-harmonic; 90.8% vs. 38.0%—harmonic—see FIG. 10 at the top). In addition, multi-frequency SCS is able to achieve comparable results (88.0% non-harmonic and 90.8% harmonic reduction vs. 88.7% and 90.8% reduction during respective single frequency stimulation) using an average frequency that is 15 Hz lower than the higher frequency of SCS (35.7% (non-harmonic) and 37.5% (harmonic) less power—see the bottom of FIG. 10). FIG. 10 illustrates Raster plots depicting comparisons of SCS efficacy (WDR neuronal output) and efficiency (average stimulation frequency) between multi-frequency SCS and conventional SCS at a fixed frequency in response to a neuropathic input. Each black line on the graph represents a time point at which a spoke is output by the WDR neuron. The output from a given pair of stimulation frequencies is compared to the output due to stimulation at the lower frequency (12 Hz, 10 Hz—top) and higher frequency (42 Hz, 40 Hz—bottom).

Figure 11A:
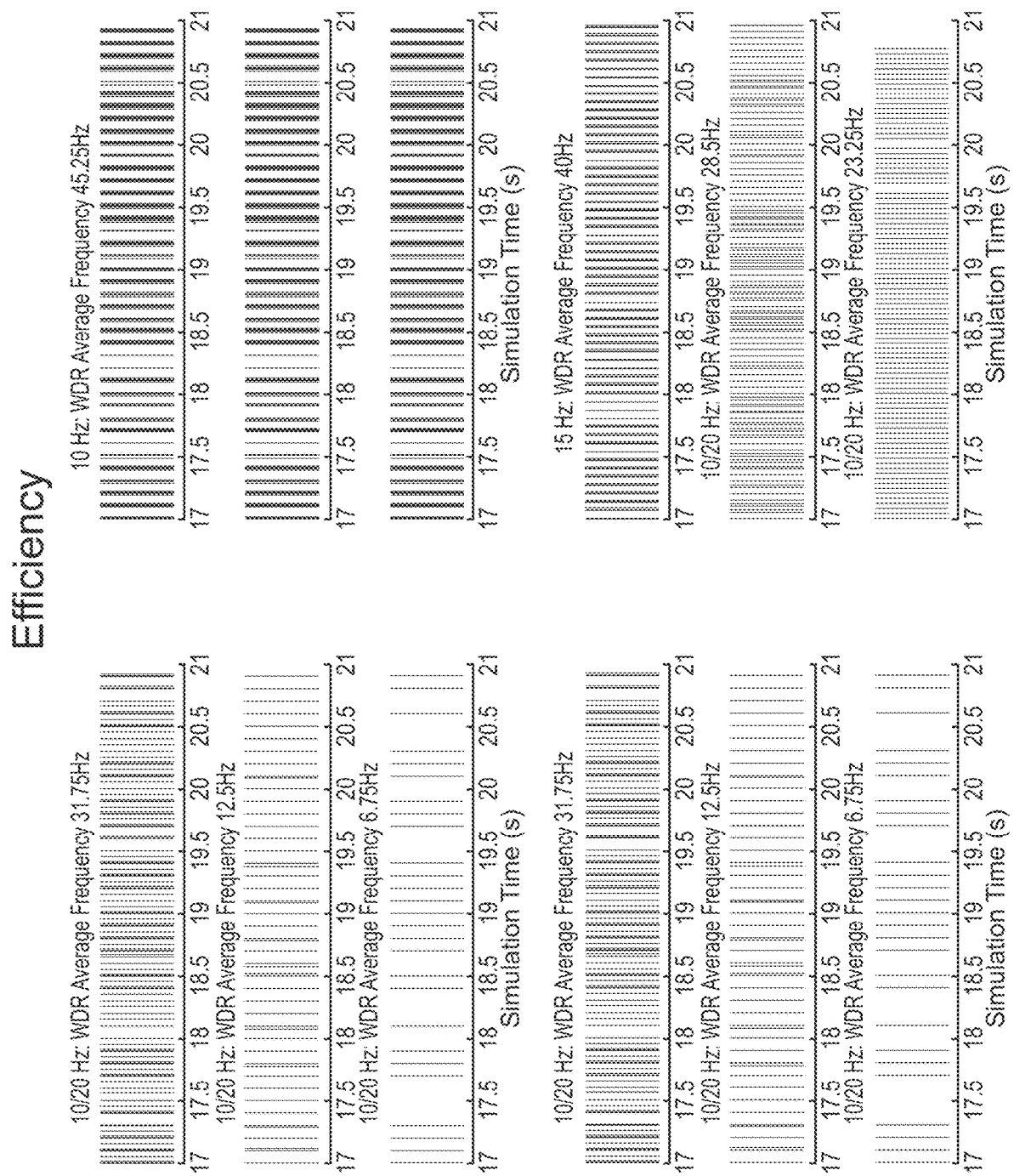
FIGS. 11A and 11B are Raster plots depicting comparisons of SCS efficacy (WDR neuronal output) and efficiency (average stimulation frequency) between several combinations of harmonic multi-frequency SCS and conventional SCS at a fixed frequency in response to a neuropathic input.
Figure 11B:
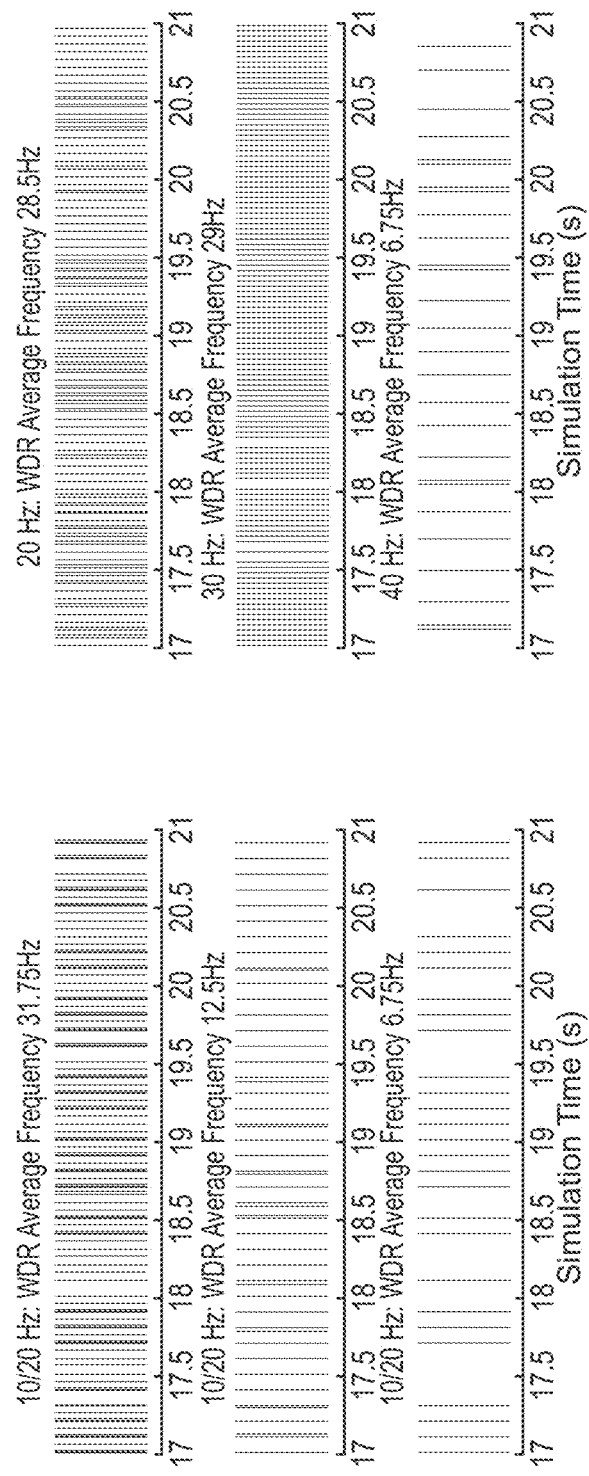

Further, it was shown experimentally that harmonic multi-frequency stimulation is both more effective and more efficient at suppressing WDR neuronal activity during a neuropathic input (see FIGS. 11A and 11B, for example). To this end, 3 combinations of harmonic SCS were tested against the neuropathic input—10/20 Hz, 10/30 Hz, and 10/40 Hz SCS—and compared efficacy (WDR neuronal output) against stimulation at the lower frequency (10 Hz) and at the average frequency (15 Hz, 25 Hz, 35 Hz) as well as efficiency against the higher frequency (20 Hz, 30 Hz, 40 Hz). In all cases, harmonic multi-frequency SCS suppressed WDR neuronal activity (i.e., is more effective) to a greater extent than single frequency stimulation at the lower frequency (56.5%—10/20 Hz; 82.9%—10/30 Hz, 88.0%—10/40 Hz versus 38.0% 10 Hz). In addition, multi-frequency SCS was also more efficient and in some cases more effective than stimulation at the higher frequency: stimulation using 10/20 Hz, 10/30 Hz, and 10/40 Hz reduced the WDR neuron's activity by 56.5%, 82.9%, and 88.0%, respectively, versus 61.0%, 60.3%, and 88% reduction by stimulation using 20 Hz, 30 Hz, and 40 Hz, but stimulation using 10/20 Hz, 10/30 Hz, and 10/40 Hz was 25.0%, 33.3%, and 37.5% more efficient than stimulation using 20 Hz, 30 Hz, and 40 Hz alone. Finally, stimulation using harmonic frequencies (i.e., single frequency stimulation using equal power consumption): 10/20 Hz stimulation suppressed WDR activity by 82.9% versus 61.0% using 20 Hz constant stimulation; 10/40 Hz stimulation suppressed WDR activity by 88.0% versus 68.2% using 25 Hz constant stimulation.

FIGS. 11A and 11B show raster plots depicting comparisons of SCS efficacy (WDR neuronal output) and efficiency (average stimulation frequency) between several combinations of harmonic multi-frequency SCS and conventional SCS at a fixed frequency in response to a neuropathic input. Each black line on the graph represents a time point at which a spike is output by the WDR neuron. The output from a given pair of stimulation frequencies is compared to the output due to stimulation at the lower frequency (10 Hz—top), average frequency (15 Hz, 20 Hz, 25 Hz—middle), and higher frequency (20 Hz, 30 Hz, 40 Hz—bottom).

In accordance with embodiments, systems and methods of the present disclosure may be implemented as an algorithm within an SCS pulse generator device. An on-board controller may deliver multiple frequencies of SCS through different output channels to different contacts on the spinal cord stimulation electrode. By virtue of stimulation through multiple contacts, different populations of axons (e.g., subpopulations of dorsal column nerve fibers) traversing the dorsal column may be activated at different frequencies, resulting in greater suppression of the neurons responsible for transmitting nociceptive information to the brain. Values of the stimulation frequencies and the electrodes through which these frequencies are delivered can be input by either a physician or a patient through a user interface. Alternatively, the device can be pre-programmed with specific combinations of frequencies to use. The applied frequencies can be multiples of each other (harmonic) or not (non-harmonic), and they may or may not be offset from each other at the start of stimulation. In addition, multi-frequency SCS may be limited to 2 frequencies, as many frequencies and axon populations as the stimulation technology will allow can be delivered to the patient. The algorithm may toggled on and off (e.g., between multi-frequency and single frequency SCS) by either the physician or patient, or it can be coupled to an internal feedback-driven algorithm for automatic control.

Figure 12:
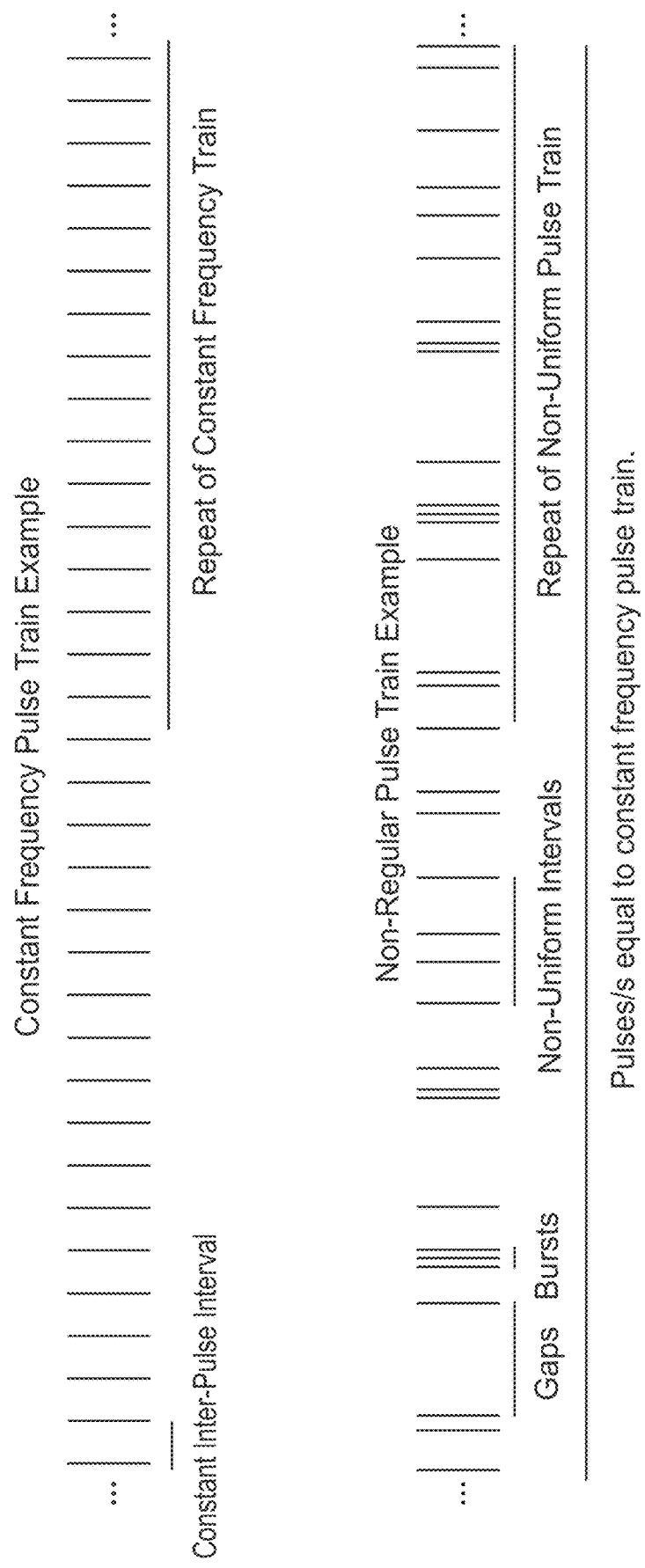
FIG. 12 is an illustration of a regular, constant frequency stimulation train wherein the interpulse intervals are constant in time and examples of non-regular temporal patterns of stimulation wherein the interpulse intervals vary in time.

FIG. 12 illustrates a regular, constant frequency stimulation train wherein the interpulse intervals are constant in time and examples of non-regular temporal patterns of stimulation wherein the interpulse intervals vary in time.

The present subject matter may be a system, a method, and/or a computer program product implemented on an SCS device, a smartphone, tablet computer, or the like. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flow chart illustrations and/or block diagrams of methods, apparatus (systems), and computer program products according to embodiments of the subject matter. It will be understood that each block of the flow chart illustrations and/or block diagrams, and combinations of blocks in the flow chart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flow chart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flow chart and/or block diagram block or blocks.

The flow chart and block diagrams in the Figures illustrate the architecture, functionality, and operation of possible implementations of systems, methods, and computer program products according to various embodiments of the present subject matter. In this regard, each block in the flow chart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration, and combinations of blocks in the block diagrams and/or flow chart illustration, can be implemented by special purpose hardware-based systems that perform the specified functions or acts or carry out combinations of special purpose hardware and computer instructions.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A method comprising:
   determining neuronal output that results from simulating concurrent delivery of a first temporal pattern of electrical stimulation for spinal cord stimulation (SCS) to a first sub-population of targeted neurological tissue of a subject and a second temporal pattern of electrical stimulation for SCS to a second sub-population of targeted neurological tissue of the subject, wherein the first sub-population of targeted neurological tissue and the second sub-population of targeted neurological tissue are different, wherein the first and second temporal patterns are determined from among other patterns for optimizing efficacy and efficiency of SCS;
   using a first electrode contact to apply the first temporal pattern of electrical stimulation to the first sub-population of targeted neurological tissue; and
   using a second electrode contact to apply the second temporal pattern of electrical stimulation to the second sub-population of targeted neurological tissue, wherein the second temporal pattern is applied concurrent to the application of the first temporal pattern.

2. The method of claim 1, further comprising:
   applying, by use of the first electrode contact, the first temporal pattern of electrical stimulation to the first sub-population of targeted neurological tissue to activate the first sub-population of targeted neurological tissue; and
   applying, by use of the second electrode contact, the second temporal pattern of electrical stimulation to the second sub-population of targeted neurological tissue to activate the second sub-population of targeted neurological tissue.

3. The method of claim 2, wherein applying the first temporal pattern of electrical stimulation comprises:
   placing the first electrode contact in electrical communication with the first sub-population of targeted neurological tissue; and
   using the first electrode contact for applying the first temporal pattern of electrical stimulation to the first sub-population of targeted neurological tissue.

4. The method of claim 3, wherein applying the second temporal pattern of electrical stimulation comprises:
   placing the second electrode contact in electrical communication with the second sub-population of targeted neurological tissue; and
   using the second contact for applying the second pattern of electrical stimulation to the second sub-population of targeted neurological tissue.

5. The method of claim 1, wherein the first and second temporal patterns of electrical stimulation are applied at different timings.

6. The method of claim 1, further comprising receiving user input for control of the application of the first and second temporal patterns of electrical stimulation.

7. The method of claim 1, wherein the frequency of the first temporal pattern of electrical stimulation is a multiple of the frequency of the second temporal pattern of electrical stimulation.

8. The method of claim 1, further comprising:
   placing the first electrode contact and the second electrode contact in electrical communication with the first sub-population and the second sub-population, respectively, of the targeted neurological tissue.

9. The method of claim 1, wherein the targeted neurological tissue comprises dorsal column nerve fibers.

10. The method of claim 1, further comprising selecting the first and second temporal patterns of electrical stimulation from among other temporal patterns for one of maximizing suppression of WDR neuron firing and minimizing average stimulation frequency.

11. The method of claim 1, further comprising selecting the first and second temporal patterns of electrical stimulation from among other temporal patterns for maximizing suppression of pain and minimizing average stimulation frequency.

12. The method of claim 1, further comprising:
selecting the first and second temporal patterns of electrical stimulation from among other temporal patterns for one of maximizing efficacy and efficiency;
minimizing average stimulation frequency is a proxy for efficiency; and
suppressing wide-dynamic range neuron firing in a prior simulation is a proxy for efficacy.

13. The method of claim 1, further comprising selecting the first and second temporal patterns of electrical stimulation from among other temporal patterns for one of minimizing patient pain and device power consumption during clinical use.

14. The method of claim 1, further comprising selecting the first and second temporal patterns of electrical stimulation from among other temporal patterns for minimizing average stimulation frequency while maintaining suppression of pain.

15. The method of claim 1, further comprising selecting the first and second temporal patterns of electrical stimulation from among other temporal patterns for optimizing efficacy and efficiency;
suppression of activity of wide-dynamic range neurons in a prior simulation (efficacy);
minimizing average stimulation frequency in a prior simulation (efficiency); and
minimizing patient pain and stimulation frequency in clinical practice.

16. The method of claim 1, further comprising:
determining the second temporal pattern of electrical stimulation based on the simulated neuronal output; and
using a pulse generator to apply electrical stimulation to the subject based on the first and second temporal patterns.

17. A system comprising:
a pulse generator;
first and second electrode contacts; and
a controller configured to:
determine neuronal output that results from simulating concurrent delivery of a first temporal pattern of electrical stimulation for spinal cord stimulation (SCS) to a first sub-population of targeted neurological tissue of a subject and a second temporal pattern of electrical stimulation for SCS to a second sub-population of targeted neurological tissue of the subject, wherein the first sub-population of targeted neurological tissue and the second sub-population of targeted neurological tissue are different, wherein the first and second temporal patterns are determined from among other patterns for optimizing efficacy and efficiency of SCS;
control the pulse generator to output an electrical signal to the first electrode contact to apply the first temporal pattern of electrical stimulation to the first sub-population of targeted neurological tissue; and
control the pulse generator to output an electrical signal to the second electrode contact to apply the second temporal pattern of electrical stimulation to the second sub-population of targeted neurological tissue,
wherein the second temporal pattern is applied concurrent to the application of the first temporal pattern.

18. The system of claim 17, wherein the first contact is configured to be in electrical communication with the first sub-population of targeted neurological tissue for application of the first temporal pattern of electrical stimulation to the first sub-population of targeted neurological tissue.

19. The system of claim 18, wherein the second electrode contact is configured to be in electrical communication with the second sub-population for application of the second temporal pattern of electrical stimulation to the second sub-population of targeted neurological tissue.

20. The system of claim 17, wherein the controller is configured to control the pulse generator to apply the multiple different frequencies of the first temporal pattern at different timings, and to apply the multiple different frequencies of the second temporal pattern at different timings.

21. The system of claim 17, further comprising a user interface for receipt of user input for control of the application of the first and second temporal patterns of electrical stimulation.

22. The system of claim 17, wherein the frequency of the first temporal pattern of electrical stimulation is a multiple of the frequency of the second temporal pattern of electrical stimulation.

23. The system of claim 17, wherein the first electrode contact and the second electrode contact are positioned in electrical communication with the first sub-population and the second sub-population, respectively, of the targeted neurological tissue.

24. The system of claim 17, wherein the targeted neurological tissue comprises dorsal column nerve fibers.

25. The system of claim 17, wherein the controller is configured to select the first and second temporal patterns of electrical stimulation from among other temporal patterns for one of maximizing suppression of WDR neuron firing (efficacy) and minimizing average stimulation frequency.

26. The system of claim 17, wherein at least one processor and memory are configured to select the first and second temporal patterns of electrical stimulation from among other temporal patterns for maximizing suppression of pain and minimizing average stimulation frequency.

27. The system of claim 17, wherein at least one processor and memory are configured to:
select the first and second temporal patterns of electrical stimulation from among other temporal patterns for one of maximizing efficacy and efficiency;
minimize average stimulation frequency in a prior simulation is a proxy for efficiency; and
suppress wide-dynamic range neuron firing in a prior simulation is a proxy for efficacy.

28. The system of claim 17, wherein at least one processor and memory are configured to select the first and second temporal patterns of electrical stimulation from among other temporal patterns for one of minimizing patient pain and device power consumption during clinical use.

29. The system of claim 17, wherein at least one processor and memory are configured to select the first and second temporal patterns of electrical stimulation from among other temporal patterns for minimizing average stimulation frequency while maintaining suppression of pain.

30. The system of claim 17, further comprising a computing device including a user interface for receipt of selection of the first and second temporal patterns.

31. The system of claim 17, wherein at least one processor and memory are configured to select the first and second temporal patterns of electrical stimulation from among other temporal patterns for optimizing suppression of activity of wide-dynamic range neurons.

32. The system of claim 17, wherein the second temporal pattern of electrical stimulation is applied to the second sub-population without activating the first sub-population of targeted neurological tissue, wherein the first sub-population of targeted neurological tissue and the second sub-population of targeted neurological tissue are different.

33. The system of claim 17, wherein the first pattern of electrical stimulation is applied to the first sub-population of targeted neurological tissue via the one or more electrode contacts to activate the first sub-population of targeted neurological tissue, and wherein the second pattern of electrical stimulation is applied to the second sub-population of targeted neurological tissue via the one or more electrode contacts to activate the second sub-population of targeted neurological tissue.

34. The system of claim 17, wherein the controller is configured to:
determine the second temporal pattern of electrical stimulation based on simulated neuronal output, and
wherein pulse generator is configured to apply the electrical stimulation to a subject based on the first and second temporal patterns.

* * * * *